United States Patent [19]

Panoz et al.

[11] Patent Number: 5,051,262

[45] Date of Patent: Sep. 24, 1991

[54] PROCESSES FOR THE PREPARATION OF DELAYED ACTION AND PROGRAMMED RELEASE PHARMACEUTICAL FORMS AND MEDICAMENTS OBTAINED THEREBY

[75] Inventors: Donald Panoz, Tuckerstown, Bermuda; Gilbert Corneille, Paris, France

[73] Assignee: Elan Corp., P.L.C., Monksland, Ireland

[21] Appl. No.: 933,287

[22] Filed: Nov. 18, 1986

Related U.S. Application Data

[63] Continuation of Ser. No. 559,431, Dec. 8, 1983, abandoned, which is a continuation-in-part of Ser. No. 287,722, Jul. 24, 1981, abandoned.

[30] Foreign Application Priority Data

Dec. 7, 1979 [FR] France .............. 79 30085

[51] Int. Cl.$^5$ .................. A61K 9/22; A61K 9/26; A61K 9/16
[52] U.S. Cl. .................. 424/468; 424/469; 424/489
[58] Field of Search .................. 424/468, 469, 489

[56] References Cited

U.S. PATENT DOCUMENTS

| 443,428 | 4/1984 | Oshlack et al. | 424/21 |
|---|---|---|---|
| 2,971,889 | 2/1961 | Swintosky | 167/82 |
| 2,993,836 | 7/1961 | Nash et al. | 147/82 |
| 3,136,692 | 6/1964 | Bandelin | 424/44 |
| 3,247,066 | 4/1966 | Milosovich | 167/82 |
| 3,330,729 | 7/1967 | Johnson | 167/82 |
| 3,499,959 | 3/1970 | Corn | 424/32 |
| 3,520,970 | 7/1970 | Lehmann | 424/25 |
| 3,538,214 | 11/1970 | Polli et al. | 424/81 |
| 3,557,279 | 1/1971 | Morse | 424/20 |
| 3,608,063 | 9/1971 | Banker | 424/22 |
| 3,629,393 | 12/1971 | Nakamoto et al. | 424/22 |
| 3,634,584 | 1/1972 | Poole | 424/21 |
| 3,653,914 | 4/1972 | Schmitt et al. | 424/44 |
| 3,676,549 | 7/1972 | Huguchi et al. | 424/44 |
| 3,764,668 | 10/1973 | Higuchi et al. | 424/44 |
| 3,835,221 | 9/1974 | Fulberth et al. | 424/20 |
| 3,882,228 | 5/1975 | Boncey et al. | 424/44 |
| 3,883,648 | 5/1975 | Ross et al. | 424/44 |
| 3,885,027 | 5/1975 | Shaw et al. | 424/44 |
| 3,917,813 | 11/1975 | Pederson | 424/20 |
| 3,954,959 | 5/1976 | Pederson | 424/21 |
| 3,961,041 | 6/1976 | Nishimura et al. | 424/44 |
| 4,079,125 | 3/1978 | Sipos | 424/35 |
| 4,083,949 | 4/1978 | Benedikt | 424/19 |
| 4,173,626 | 11/1979 | Dempski et al. | 424/19 |
| 4,181,708 | 1/1980 | Dannelly | 424/19 |
| 4,196,187 | 4/1980 | Dannelly | 424/21 |
| 4,199,560 | 4/1980 | Gyarmati | 424/19 |

(List continued on next page.)

FOREIGN PATENT DOCUMENTS

| 106443 | 8/1982 | European Pat. Off. . |
|---|---|---|
| 2336218 | 2/1975 | Fed. Rep. of Germany . |
| 2741755 | 3/1978 | Fed. Rep. of Germany . |
| 2950977 | 12/1978 | Fed. Rep. of Germany . |
| 2743183 | 4/1979 | Fed. Rep. of Germany . |
| M7392 | 12/1969 | France . |
| 2223047 | 10/1974 | France . |
| 2353285 | 12/1977 | France . |

(List continued on next page.)

OTHER PUBLICATIONS

Gibaldi, M.: Biopharmaceutics and Clinical Pharmacokinetics. Lea and Febiger, Philadelphia, 1977 (2nd Ed.).
Harris, P.A. and Riegelman, S.: J. Pharm. Sci., 58(1):71, 1969.
Gibaldi, M., Boyes, R.N. and Feldman, S.: J. Pharm. Sci., 60(9):1338, 1971.
Scheline, R.R.: Pharmacol. Rev., 25(4):451, 1973.
Conolly, M.E., Davies, D.S., Dollery, C.T., et al.: Br. J. Pharmac., 46:458, 1972.
Brunk, S.F., and Delle, M.: Clin. Pharmacol. Ther., 16(1):51, 1974.
Gibaldi, M. and Perrier, D.: Drug Metab. Rev., 3(2):185, 1974.
Goldman, P.: N. Engl. J. Med., 289(12):623, 1973.
Shand, D.G. and Rangno, R.E.: Pharmacol., 7:159, 1972.
Paterson, J.W., Conolly, M.E., Dollery, C.T., Hayes, A. and Cooper, R.G.: Pharmacol. Clin., 2:127, 1970.
Evans, G.H. and Shand, D.G.: Clin. Pharmacol. Ther., 14(4):494, 1973.
Nies, A.S. and Shand, D.G.: Circulation, 52:6, 1975.
Regårdh, C.G., Borg, K.O., Johansson, R., Johansson, G., and Palmer, L.: J. Pharmacokin. Biopharm., 2(4):347, 1974.
Gibaldi, M.: J. Pharm. Sci., 64(6):1035, 1975.

(List continued on next page.)

Primary Examiner—Frederick E. Waddell
Attorney, Agent, or Firm—Robert H. Falk; Henry Croskell; Harry J. Watson

[57] ABSTRACT

Specifically, the present invention relates to processes for preparing delayed action galenic forms. The process is characterized in that the application solutions of excipients, coatings and active constituents are adjusted to a desired pH. The independence of the rate of dissolution of a controlled release or sustained action oral pharmaceutical form is increased by admixing a pH adjusting agent with every application solution of medicament, excipeint or coating, throughout the course of formulation of the pharmaceutical form.

16 Claims, 10 Drawing Sheets

U.S. PATENT DOCUMENTS

| | | | |
|---|---|---|---|
| 4,206,214 | 6/1980 | Harker et al. | 424/251 |
| 4,248,872 | 2/1981 | Horrobin | 424/251 |
| 4,261,969 | 1/1981 | Heller | 424/19 |
| 4,265,874 | 5/1981 | Bonsen et al. | 424/44 |
| 4,267,138 | 5/1981 | Dobo et al. | 264/117 |
| 4,289,751 | 9/1981 | Windheuser et al. | 424/44 |
| 4,341,563 | 7/1982 | Kurihara et al. | 106/71 |
| 4,341,759 | 7/1982 | Bogentoft et al. | 424/21 |
| 4,344,929 | 8/1982 | Bonsen et al. | 424/44 |
| 4,361,546 | 11/1982 | Stricker | 424/19 |
| 4,367,217 | 1/1983 | Gruber et al. | 424/19 |
| 4,427,648 | 1/1984 | Brickl | 424/16 |
| 4,432,965 | 2/1984 | Keith et al. | 424/19 |
| 4,434,152 | 2/1984 | Horvath et al. | 424/19 |
| 4,459,279 | 7/1984 | Stricker et al. | 424/19 |
| 4,460,563 | 7/1984 | Calachi | 424/35 |
| 4,483,846 | 1/1984 | Koide et al. | 424/19 |
| 4,499,093 | 2/1985 | Galabov et al. | 514/258 |
| 4,521,401 | 6/1985 | Dunn | 424/19 |
| 4,572,833 | 2/1986 | Pederson et al. | 424/20 |
| 4,578,264 | 3/1986 | Stricker et al. | 424/37 |
| 4,606,909 | 8/1986 | Bechgaard et al. | 424/21 |
| 4,663,150 | 5/1987 | Panoz et al. | 424/494 |
| 4,713,248 | 12/1987 | Kjorn et al. | 424/468 |
| 4,716,040 | 12/1987 | Panoz | 424/497 |
| 4,716,041 | 12/1987 | Kjornaes et al. | 424/468 |
| 4,721,619 | 12/1987 | Panoz | 424/459 |
| 4,726,951 | 12/1987 | Panoz | 424/465 |

FOREIGN PATENT DOCUMENTS

| | | |
|---|---|---|
| 2390959 | 12/1978 | France . |
| 2401619 | 3/1979 | France . |
| 862376 | 3/1961 | United Kingdom . |
| 1139869 | 1/1969 | United Kingdom . |
| 1139991 | 1/1969 | United Kingdom . |
| 1510370 | 5/1978 | United Kingdom . |
| 2025227A | 1/1980 | United Kingdom . |
| 2039737 | 8/1980 | United Kingdom . |
| 2067073A | 7/1981 | United Kingdom . |

OTHER PUBLICATIONS

Wilkinson, G.R. and Shand, D.G.: Clin. Pharmacol. Ther., 18(4):377, 1975.

Woodcock, B.G., Loh, W., Habedank, W. and Rietbrock, N.: Clin. Pharmacol. Ther., 32(5):622, 1982.

Assinder, D.F., Chasseaud, L.F., Hunter, J.O., Jung, R.J., and Taylor, T. Arzneim Forsch./Drug Res., 27:156, 1977.

Assinder, D.F., Chasseaud, L.F. and Taylor, T.: J. Pharm. Sci., 66(6):775, 1977.

Zylber-Katz, E., Koren, G., Granit, L. and Levy, M.: Biopharm. Drug Dis., 5:109, 1984.

Woodcock, B.G., Schulz, W., Kober, G. and Rietbrock, N.: Clin. Pharmacol. Ther., 30(1):52, 1981.

Gilmore, I.T. and Hoffman, A.F.: Gastroenterology, 78(1):177, 1980.

Ueda, C.T., Williamson, B.J. and Dzindzio, B.S.: Clin. Pharmacol. Ther., 20(3):260, 1978.

Levy, G., Leonards, J.R., and Procknal. J.A.: J. Pharm. Sci., 54(12):1719, 1965.

Nelson, E.: J. Am. Pharm. Assoc. (Sci. ed.), XLVII(4):297, 1958.

Juncher, H. and Raaschou, F.: AM&CT, IV(9):497, 1957.

Anderson, K.W.: Arch. Int. Pharmacodyn., 147(1-2):171, 1964.

Epstein, L.C. and Lasagna, L.: J. Pharmacol. Exp. Ther., 164(2):433, 1968.

Hogben, C.A.M., Schanker, L.S., Tocco, D.J. et al.: J. Pharmacol. Exp. Ther., 120:540, 1957.

Schanker, L.S.: J. Med. Pharm. Chem., 2(4):343, 1960.

Hogben, C.Q.M., Tocco, D.J., Brodie, B.B., et al.: J. Pharmacol. Exp. Ther., 125:275, 1959.

Shore, P.A., Brodie, B.B., Hogben, C.A.M.: J. Pharmcol. Exp. Ther., 119:361, 1957.

Travell, J.: J. Pharmacol. Exp. Ther., 69:21, 1940.

Bradley, W.B., Schnedorf, J.G. and Ivey, A.C.: Am. J. Digest. Dis. & Nut., 3:415, 1936.

Schanker, L.S., Tocco, D.J., Brodie, B.B., et al.: J. Pharmacol. Exp. Ther., 123:81, 1958.

Levine, R.R.: Digest. Dis., 15(2):171, 1970.

Truitt, E.B., Jr. and Morgan, A.M.: J. Pharm. Sci., 53(2):129, 1964.

Barr, W.H., Adir, J. and Garrettson, L.: Clin. Pharmacol. Ther., 12(5):779, 1971.

Lim, C.C., Presbury, D.G.C. and Adamson, J.: Practitioner, 212:728, 1974.

Manners, B.T.B., Grob, P.R. and Gibbs, J.: Brit. J. Clin. Practice, 26(3):129, 1972.

Pines, A., Greenfield, J.S.B., Raafat, H., Sreedharan, K.S., Khaja G. and Linsell, W.D.: Brit. J. Clin. Practice, 26(10):475, 1972.

Perera, P.M.: Brit. J. Vener. Dis., 51:333, 1975.

Lucas, C.R., Mugglestone, C.J. and Thomas D.R.: J. Int. Med. Res., 5:124, 1977.

Corrigan, O.I., Dunne, A. McLaughlin, J., Geoghegan, E.J., Killian, C.A. and Panoz, D.E.: p. 163. Marcel Dekkler, Inc., New York and Basel, 1983.

Siurala, M., et al.: Scand. J. Gastroent., 4:269, 1969.

George, C.F.: Clin. Pharmacokin., 4:433, 1979.

Chasseaud, L.F., Down, W.H. and Grundy, R.K.: Europ. J. Clin. Pharmacol., 8:157, 1975.

Smith, S.S. and Rawlins, M.D.: Variability in Human Drug Response. Butterworths and Co., London, 1976 (2nd Ed.).

George, C.F., Orme, M.L., Buranapong, P., Macerlean, D., Breckenridge, A.M. and Dollery, C.T.: J. Pharmacokin, Biopharm., 4(1):17, 1976.

Davies, D.S., George, C.F., Blackwell, E., et al.: Br. J. Clin. Pharmac., 1:129, 1974.

Gibaldi, M.: Biopharmaceutics and Clinical Pharmacokinetics. Lea and Febiger, Philadelphia, 1979 (1st Ed.).

Furesz, S.: Antibiot, Chemother., VIII(9):446, 1958.

Downer, H.D., Galloway, R.W., Horwich, L. and Parke, D.V.: J. Pharm. Pharmac., 22:479, 1970.

Åsberg, M., Evans, D.A.P. and Sjöqvist, F.: Chem.-Biol. Interactions, 3:238, 1971.

Ochs, H.R. and Kölle, E.U.: Drug, Dev. Eval., 9:225, 1983.

(List continued on next page.)

OTHER PUBLICATIONS

Varro, V.: Ther. Hung., 15:3, 1967.
Ramsch, K. D., "Zur Pharmakokinetik von Nifedipin", S.,. 4, Heft 4:55–61 (1981).
Urquhart, J., "Controlled-Release Pharmaceuticals", APS Section of Pharmacology and Toxicology at the 27th National Meeting of the Academy of Pharmaceutical Sciences, Kansas City, MO (11/79).
Cabana, B., "Regulatory Consideration in Transdermal Controlled Medication", Drug Development Industrial Pharmacy, 9(4), 707–724 (1983).
Kala and Dittgen, "In Vitro and In Vivo Availability of the Active Prinicples From Acrylic Polymer-Based Capsules", pp. 7–17.
Brunnengraeber, Chem. Abstr. 76 #27955W-Drug Filled Capsules.
Imhof, Chem. Abstr. 85 #130521m "Pharmaceutical Preparations for Prophylactic and Therapeutic Treatment of Coronory Heart Disease"
Dittgen, Chem. Abstr. 85 #198123p "Preparation and In Vitro Testing of Polyacrylate-Based Bead-Polymerizates Containing Pharmaceutically Active Ingredients".
Dittgen, Chem. Abstr. 87 #189376n "Preparation an In Vitro Testing of Polyacrylate-Based Polymers Containing . . ."
Dittgen, "Poliakrilat alapu gyogryszerhatoanyag-tartalmu gyongy-polimerizatumok eloallitasa es in vitro vizsgalata", 20. evfolyam 7 szam.
Miyata, Chem. Abstr. 86 #65806n "Polynuclear Complex Compound".
Corneille, Chem. Abstr. 87 #206519f "Pharmaceutically Administratable Form of Vincamine and Its Derivatives".
Galeazzi, Chem. Abstr. 88 #11845x "The Effect of an Antacid on the Bioavailability of Indomethcin".
Buchanan, Chem. Abstr. 88 #146179d "Assessment of Antithrombotic Drugs Ex Vivo and In Vivo.
Dittgen, Chem. Abstr. 89 #12078g "Drug Release From Embedding Forms Based on Polyacrylate".
Dittgen, Chem. Abstr. 89 #30644t "Study on in Vitro Drug Release From Polyacrylate-Based Bead Polymerizates".
El-Sabbagh, et al., Chem. Abstr. 89 #169017j "Solubilization of Indomethacin".
Gittgen, et al., Chem. Abstr. 90 #76473k "In Vitro and In Vivo Availability of the Active Principles From Acrylic Polymer-Based Beads".
Prugnand, Chem. Abstr. 91 #18147e "Composition Containing Pyrimidopyrimidine Derivative and Acetylsalicyclic Acid".
Vignon, et al., Chem. Abstr. 92 #82302m "Bioavailability of Indomethacin. Study of a Delayed-Release Formula".
Panoz, et al., Chem. Abstr. 93 #225639k "Oral Formulations With Programmed Action".
Volpi, et al., Chem. Abstr. 94 #36188x "Therapeutic Doses and Physicochemical Constants of Bases and Acids".
Kawata, et al., Chem. Abstr. 94 #127383y "Continuously Releasing Pharmaceutical Preparation of a Solid Drug Material".
Astier, et al., Chem. Abstr. 95 #225564y "Relative Bioavailability of a Sustained Release Indomethacin, Compared to Conventional Immediate Action Preparation".
Elan Reviews "Evaluation of Antibiotic Therapy, A New Perspective (c. 1980).
Panoz, "Innovation and Creativity in The Design of New Pharmaceutical Disage Forms", 1981 Symposium.
Corrigan, et al., "Development of a Controlled Absorption Ouinidine Drug Delivery System", publ. Controlled Release Delivery Systems, Roseman & Mansdorf, (Chap. 12), pp. 163–167 (1983).
Evers, "Getting Drugs Into Your Bloodstream", publ. Technology Ireland, (April 1982).
Elan Brochure, 2d Ed.
Perucca, et al., "Pharmacokinetic and Pharmacodynamic Studies With a New Controlled-Release Formulation of Propranolol in Normal Volunteers: A Comparison With Other Commercially Available Formulations", B.J. Clin. Pharmac. 18 at 37–43 (1984).
Bottini, et al., "Comparative Oral Bioavailability of Conventional Propranolol Tablets and a New Controlled Absorption Propranolol Capsule", Drug Dev. and Ind. Pharm. 9 (8) at 1475–1493 (1983).

PROCESSES FOR THE PREPARATION OF DELAYED ACTION AND PROGRAMMED RELEASE PHARMACEUTICAL FORMS AND MEDICAMENTS OBTAINED THEREBY

CROSS-REFERENCED RELATED APPLICATIONS

The present application is a continuation of U.S. Ser. No. 559,431, filed Dec. 8, 1983, which is a continuation of U.S. Ser. No. 287,722, having a U.S. filing date of July 24, 1981, now abandoned, with a PCT international filing date of Dec. 5, 1980, the entire contents of which are hereby incorporated by reference.

FIELD OF THE INVENTION

The process is characterized in that the application solutions of excipients, coatings and active constituents are adjusted to a desired pH. Likewise, the present invention relates to improvements in or processes for the preparation of various pharmaceutical forms of medicaments with delayed action, and particularly, to processes for the preparation of tablets, granules, and the like, with delayed action and programmed release.

BACKGROUND OF THE INVENTION

Much progress has been made in recent years in the preparation of forms for oral administration of medicaments with a view toward better control of the kinetics of release of medicament. Coating materials have been developed, as have manners to retain the medicament in inert matrices and manners for diffusion or controlled dialysis of medicaments. Recourse has even been had to the combination of several of these forms to ensure, starting from the same pharmaceutical form, a modification of the absorption or of the elimination of the medicaments in order to prolong the time of action thereof, as in the case, for example, of the association in the same medicament of viscosifying agents which retard the dissolving process with active constituents of well determined granulometry. The improvements which have been introduced in the preparation of pharmaceutical forms for oral administration with a prolonged action, are manifested principally (1) in a fractionation in the same medicament unit (capsule, tablet, granule) of the total dose into several small doses coated with suitable excipients which are made available to the organism at the desired time, (2) in the retention of the medicament in a sort of inert matrix which is very slowly splittable, in a form which is called upon to diffuse its contents gradually according to predetermined kinetics, and (3) in the fixing of the medicaments to several adjuvants so as to obtain insoluble complexes from which the medicaments are eluted slowly and supplied to the organism according to predetermined kinetics.

The various coatings and coating films depend evidently on the physiological factors (enzymatic activity, pH, etc.) which exist in the gastro-intestinal tract; these factors (and more particularly, the pH) vary not only throughout the gastro-intestinal tract, but also from one person to another. The possibility of controlling the release of the active principle throughout the course of the medicament in the gastro-intestinal tract assumes the first place that it is possible to control the solubility of the medicament at each moment of this process. The solubility of the majority of medicaments (if not all) varies precisely as a function of the pH.

Until now, the addition of application solutions of excipients and of coatings, constituted by polyvinylpyrrolidone, gum-lacquer, waxes, syrups, etc., has been used as a means for moistening the pellets or tablets of sugar or the pellets and/or the tablets of active principle to cause the adherence thereto of subsequent layers of active component. It is precisely by the modification of these application solutions that the object envisaged by Applicant has been obtained.

To overcome this drawback, it has been known to add a solid pH adjusting compound to the active component in an attempt to adjust the pH around the medicament and improve the release of the active principle. However, except in the case of granules obtained by high compression (see British patent 2,039,737), this solid product does not exert its action completely in vivo since the dissolution into the stomach is not always complete and steady so that the drug is already absorbed through the gastro-intestinal tract when the optimum pH is finally attained in the stomach.

SUMMARY OF THE INVENTION

It is accordingly an object of the present invention to further improve the process of the preparation of pharmaceutical forms for oral administration of medicaments with prolonged action and programmable kinetics.

It is a further object of the present invention to provide a process for the preparation of such forms of administration so as to be able to dispense with high compression.

It is yet another object of the present invention to provide a process for the preparation of such forms of administration which reduces the cost price of these extremely widespread pharmaceutical forms.

It is yet another object of the present invention to provide forms of medicaments for oral administration in which the solubility of the medicament is maintained substantially constant regardless of the pH of the particular portion of the gastro-intestinal tract through which the medicament is moving at any given point in time.

It is also an object of the invention to provide novel galenic forms obtained according to the process of the present invention.

The results obtained are spectacular both from the point of view of kinetics of release of the active substance, which are, besides, bound together.

It is another object of the present invention to provide a medicament for oral administration which will provide an improved blood level profile of the medicament with time.

Yet another object of the present invention is to provide a pharmaceutical form for medicaments for oral administration in which acid unstable drugs are protected from acid hydrolysis in the stomach.

These and other objects in accordance with the present invention are obtained by creating a micro-environment surrounding the medicament throughout its course in the gastro-intestinal tract which will permit optimum solubility regardless of the pH of the portion of the tract in which the medicament is passing. Such a micro-environment is obtained by adding an appropriate pH-adjusting agent to every layer of medicament, and preferably to every application solution and coating applied to the dosage form.

Accordingly, a chief embodiment of our invention is directed to a process for the preparation of delayed-action galenic forms, wherein the forms, wherein the solutions for applying excipients, coatings and active constituents are adjusted to a desired pH. Further the invention is directed to the same process, wherein the application solutions are adjusted either depending on the medicament chosen, (1) to an alkaline pH by means of organic and/or inorganic bases and/or basic salts, or (2) to an acid pH by means of organic acids and/or acid salts. Still further, an embodiment of our invention is directed toward galenic forms obtained according to the processes described in this chief embodiment.

BRIEF DESCRIPTION OF THE DRAWINGS

The present invention will be better understood from a consideration of the following description of preferred embodiments and the appended drawings, in which.

DETAILED DESCRIPTION OF PREFERRED EMBODIMENTS

According to the present invention there is provided a process for the preparation of pharmaceutical forms with delayed action, characterized in that the application solutions of the excipients, of the coatings and of the active constituients are adjusted to a desired pH. This adjustment of the pH of the application solutions has the effect of more uniformly modifying the pH of the environment inside the pellet, the tablet or the like by countering the hostile environment which exists outside of the pellet, of the tablet or the like. In an advantageous embodiment of the process according to the invention, the application solutions are adjusted to an alkaline pH by means of organic and/or inorganic bases and/or basic salts. According to another advantageous embodiment of the process according to the invention, the application solutions are adjusted to an acid pH by means of organic acids and/or acid salts.

The description which follows refers to examples of manufacture of the novel galenic form, to comparison tests of solubilities as well as to clinical tests of determination of the levels of medicaments in the blood.

It must of course be understood however that these examples and clinical tests are given solely by way of illustration of the process and product according to the invention, of which they do not constitute a limitation thereof in any way.

One of the factors affecting the blood levels of a drug is its solubility in the pH environment in which it finds itself in the gastro-intestinal tract after oral administration. If the drug is poorly soluble, it will be poorly absorbed from the gastro-intestinal tract into the blood. Many drugs are either weakly acidic or alkaline. The solubility of a weak acid or base usually varies considerably as a function of pH, and the pH of the gastro-intestinal tract varies from very acidic pH values in the stomach to slightly alkaline values in the small intestine. The solubility of weak acids is greatest in alkaline solution, whereas the solubility of weak bases is greatest in acidic solutions.

According to the present invention, a dosage form is produced in such a manner that a pH-adjusted microenvironment is created in which the solubility of the drug is maintained substantially constant. This results in an improved blood level profile.

A second situation in which the creation of a pH-adjusted micro-environment results in an improved blood level profile is where a drug is unstable in the acid pH found in the stomach. A dosage form in accordance with the present invention, in which a pH-adjusted micro-environment is created protects the acid-unstable drugs from acid hydrolysis in the stomach.

The present invention creates such a pH-adjusted micro-environment, preferably, by causing the pH of all coating solutions to be adjusted, as well as the pH of every application solution, and every layer of active component. In conventional dosage forms, it is common to use a pellet or tablet of sugar as the core, or a tablet of active principle as a core, to which are applied application solutions of excipients and coatings such as polyvinyl pyrrolidone, gum lacquer, waxes, syrups, etc., as a means for moistening the pellets or tablets to cause the adherence thereto of subsequent layers of active component. In accordance with the present invention, the core sugar pellet need not have pH-adjusting agent added thereto, as long as the innermost layer or tablet of active principle has pH-adjusting agent added thereto, and, preferably, all other application solutions and coating solutions added thereto. Thus, the desired pH environment will be maintained throughout the travel of the drug through the gastro-intestinal tract. This adjustment of the pH of the application solutions has the effect of more uniformly modifying the pH of the environment inside the pellet, the tablet or the like, by countering the hostile environment which exists outside of the pellet, the tablet, or the like.

The type of pH-adjusting agent, i.e., mildly acidic or mildly basic, will depend on the particular drug of the active principle. If the active principle is weakly alkaline, then the pH is adjusted with an acidic pH adjustor. If the active principle is weakly acidic or is a drug which is unstable in the acid pH environment found in the stomach, then the pH-adjusting agent should be a base. Of course, the principle of the present invention would not be applicable to drugs which do not have different solubilities at different pH's, and which are not subject to acid hydrolysis.

Examples of drugs which are mildly basic and whose blood level profile will be improved by use of an acidic pH adjustor added, preferably, to all solutions of the excipients, coatings, and active constituents, include cephalexin, cephalothin, methyldopa, cefazolin, propanolol, doxycycline, amoxycillin, dipyridamole, propoxyphene, ampicillin, lincomycin, vincamine, clonidinine, glafenine, disopyramide, clorazepate, cephalosporins, rifamycin and quinidine sulfate. This list is not intended to be complete and those skilled in the art will understand that any active principle which is a basic drug, would have its release characteristics improved in accordance with the present invention using an acidic pH adjustor.

Examples of drugs which are weak acids or which are subject to acid hydrolysis to which a basic pH adjustor would be added, preferably, to every application solution of excipient, coating and active constituent include diazepam, cimetidine, indomethacin, ibuprofen, furosemide, spironolactone, erythromycin, gentamicin, diclofenac, glibenclamide, althazide, naproxen, allopurinol, sulfamethoxazole, prosultiamine, betamethasone, troleandomycin, clometacin, sulpiride, oxyphenbutazone, and sulindac. Again, this list is not intended to be all inclusive, and those of ordinary skill in the art would recognize whether any given drug is subject to acid hydrolysis or is a basic drug, in which case its blood profile characteristics could be improved in accordance with the present invention by using an alkaline pH adjustor.

Typical pH adjusting agents which may be used in accordance with the present invention include any non-toxic acid, particularly the organic acids, such as citric acid, maleic acid, tartaric acid, fumaric acid, etc., or acidic salts. Similarly, any non-toxic basic substance may be used as the alkaline pH adjustor, including alkaline salts of organic acids, alkaline carbonates, alkaline bicarbonates, etc. The present invention must not be limited to the particular pH adjustment agents discussed herein as those skilled in the art understanding the concept of the present invention would readily know whether any given compound would be operable as a pH-adjusting agent in accordance with the present invention.

As is common in the art, the formulations of the present invention will generally include a dissolution controller which determines the rate at which the drug is released. Some well known dissolution controllers include polyvinyl pyrrolidone, polyvinyl acetate phthalate, cholesteryl acetate, glucose, shellac, cellulose, ethyl cellulose, the methacrylates, the acetophalates, etc.

The amount of pH-adjusting agent to be added will depend upon the particular medicament, as well as the size of the dosage formulation. Ideally, as much pH adjusting agent as possible should be added, as the more pH-adjusting agent present, the better ability there is to maintain constant solubility properties. In practice, however, it is not possible to add as much pH-adjusting agent as would be desirable, and so as much is added as possible, given the size and weight constraints of the unit dosage. It is preferred that the pH adjusting agent be added to every application solution, coating and layer or core of active principle used in formulating the tablet or capsule, starting with the innermost layer or core of active principle. Every such layer or application solution must have the same type of pH adjustor (acid or alkaline), and, preferably, the same pH-adjusting agent.

The process of the present invention is applicable to any known process of making delayed action or controlled release medicaments. For example, one well-known method of making such formulations is to start with a sugar granule which is coated with active principle by means of an application solution, and which is then coated with a desired number of layers of delayed release coating. In other processes, multiple layers of pharmaceuticals are applied, possibly with layers of delayed release material therebetween. The dosage unit may be built up into a single tablet, or may be made into a plurality of granules which are administered together in the form of a capsule. Any of these known methods may be used in accordance with the present invention, including any known dissolution controller, coating agent, delayed release material, etc., with the proviso that in accordance with the most preferred embodiment present invention, every layer of the active principle, every application solution applied, every solution of coating, etc., starting with the innermost layer of active principle, must have a pH-adjusting agent added thereto, so that the micro-environment of the active principle will immediately attain the desired pH and this desired pH will be maintained throughout the course of travel of the drug through the gastro-intestinal tract.

The following examples and the graphs which relate thereto and are shown in the accompanying drawings illustrate methods and products in accordance with the present invention. It must be understood that the present invention is not intended to be limited to the materials used in the following examples.

EXAMPLE 1

Quinidine sulphate is a salt of a basic drug. As such it is more soluble in an acidic environment than in a basic environment. Without a pH-adjusting agent the solubility of this drug in alkaline solutions, and hence in the small intestine (where most absorption takes place), is low. The addition of an acidic pH-adjusting agent therefore increases the area of the gastro-intestinal tract over which the drug is absorbed and thus improves the blood level profile.

Quinidine sulfate (1,500 g), citric acid (750 g), and talc (100 g) are mixed intimately, and the mixture is coated onto non-pareil seeds (0.5-0.6 mm) of sugar with solution A. Solution A is a mixture of 1:1:16 (W/W/V) polyvinylpyrrolidone (PVP)/citric acid/isopropyl alcohol. Several coats of 90:10 (V/V) mixture of solutions B and C are then applied to achieve the desired solubility profile. Solution B comprises 33:7:60 (W/W/V) shellac/citric acid/industrial methylated spirits. Solution C comprises 20:10:70 (W/W/V) PVP/citric acid/isopropyl alcohol.

EXAMPLE 2

Quinidine sulphate (3,000 g), fumaric acid (1,200 g) and talc (200 g) are mixed intimately, and the mixture is coated onto non-pareil seeds (0.4-0.5 mm) using a 90:10 (V/V) mixture of solutions D and E, where solution D is 10:10:80 (W/W/V) PVP/fumaric acid/isopropanol, and solution E is 16.5:8.5:75 (W/W/V) shellac/fumaric acid/industrial methylated spirits.

Several coats of a 5:95 (V/V) mixture of solutions D and E respectively are then applied to achieve the desired solubility profile.

COMPARATIVE EXAMPLE 3

A non-pH adjusted product is made in the same way as set forth in Example 2 above, with the exclusion of fumaric acid.

EXAMPLE 4

1,500 g erythromycin base, 30 g explotab A (a starch derivative also known as primogel) and 1,020 g sodium citrate are mixed intimately. This mixture is ground finely with 950 ml of a solution made up of 47 g of PVP and 50 g of sodium citrate made up to 950 ml with isopropyl alcohol. The resulting mixture is ground finely with 125 ml of 0.5:1:2 (W/W/V) sodium citrate/cholesteryl acetate/isopropyl alcohol solution. The mixture is then dried at 45° C. and fitzmilled through a 30 mesh screen. The milled granulation is then compressed into slugs which are fitzmilled and screened between No. 30 and No. 12 mesh.

COMPARATIVE EXAMPLE 5

A non-pH adjusted product is made in the same manner, except for the exclusion of sodium citrate (i.e., the pH-adjusting agent).

EXAMPLE 6

1,000 g dipyridamole, 500 g citric acid, 500 g fumaric acid, and 200 g talc are mixed intimately. The mixture is coated onto non-pareil seeds (0.6-0.7 mm) using a 50% sucrose, 25% citric acid solution in water. Several coats of 50:50 mixture of PVP solution and shellac solution diluted two times with isopropanol and with 50% talc suspended in it are then applied to achieve the desired solubility profile. The PVP solution used above comprises 20:10:70 (W/W/V) PVP/citric acid/isopropanol. The shellac solution referred to above comprises 33:7:60 (W/W/V) shellac/citric acid/industrial methylated spirits.

COMPARATIVE EXAMPLE 7

A non-pH adjusted product was made in the same manner as set forth in Example 6 with the exclusion of citric acid and fumaric acid.

EXAMPLE 8

1,500 g of alpha-methyldopa and 1,250 g of citric acid are mixed and blended, and the mixture is coated onto non-pareil seeds (0.5-0.6 mm) with a solution of 5% polyvinyl pyrrolidone in isopropyl alcohol containing 1.5% citric acid. When all of the dried application powder is applied to the non-pareils using the pH-adjusted application solution, the pills are tray dried at 36° C. for 12 hours and then a pH-adjusted controlled release solution is applied. The controlled release solution comprises 1 part by volume 20% polyvinyl pyrrolidone in isopropyl alcohol, 10 parts by volume isorpopyl alcohol, 9 parts by volume 33.66% shellac in ethanol, 10 parts by weight talc, and 1.5 parts by weight citric acid. The controlled release solution is applied until the finished granules, using the USP XX dissolution apparatus No. 2 at 75 rpm, have a dissolution rate of 10-45% in 1 hour, and 45-90% in 3 hours.

EXAMPLE 9

2,000 g of propranolol HCl, 1,000 g of fumaric acid and 200 g of talc are mixed intimately, and the mixture is coated onto non-pareil seeds with an application solution comprising 90 parts of 20% polyvinyl pyrrolidone in isopropyl alcohol, and 10 parts of 33.66% shellac in ethanol containing 2% fumaric acid.

When all of the dried application powder is applied to the non-pareils using the pH-adjusted application solution, the pills are tray dried at 36° C. for 12 hours and then the pH-adjusted controlled release solution described in Example 8 is applied until the finished granules using the USP XX dissolution apparatus No. 2 at 75 rpm have a dissolution rate of 0-10% after 1 hours, 15-40% after 4 hours, 70-90% in 8 hours, and over 90% in 12 hours.

EXAMPLE 10

1,000 g diltiazem HCl, 250 g fumaric acid and 100 g talc are mixed and blended. The mixture is coated onto 500 g of non-pareil seeds (0.5-0.6 mm) by means of a pH adjusted application solution comprising 80 parts of 10% polyvinyl pyrrolidone in isopropyl alcohol and 20 parts of 16.5% shellac solution in ethanol containing 2% fumaric acid. When all of the application powder has been applied tot he non-pareils using the pH-adjusted application solution, the pills are tray dried at 36° C. for 12 hours, and then pH-adjusted controlled release solution is coated thereon. The pH-adjusted time release solution is the same as that described above in example 8, but using 4 parts fumaric acid in place of citric acid. The controlled release solution is applied until the finished granules, using the USP XX dissolution apparatus No. 2 at 75 rpm, have a dissolution rate of less than 10% in 2 hours, 10-40% in 4 hours, 40-70% in 8 hours, and greater than 90% in 12 hours.

EXAMPLE 11

1 kg of indomethacin, 1 kg of sodium citrate and 0.050 kg of talc were mixed intimately. This mixture was ground finely and then by means of an application solution according to the invention composed of saccarose (50%) and sodium citrate (20%), it was applied to granules of about 0.4 mm diameter (0.5 kg). It was dried and sieved to remove the granules which were too small or too large and it was coated by means of an isopropanol solution containing 20% of polyvinyl pyrrolidone and 33% of gum-lac.

EXAMPLE 12

The procedure was similar to that described in Example 11, except that dipyridamole was mixed with citric acid and the application solution contained 20% of citric acid beside the saccharose (50%).

EXPERIMENT 1

Figure 1:
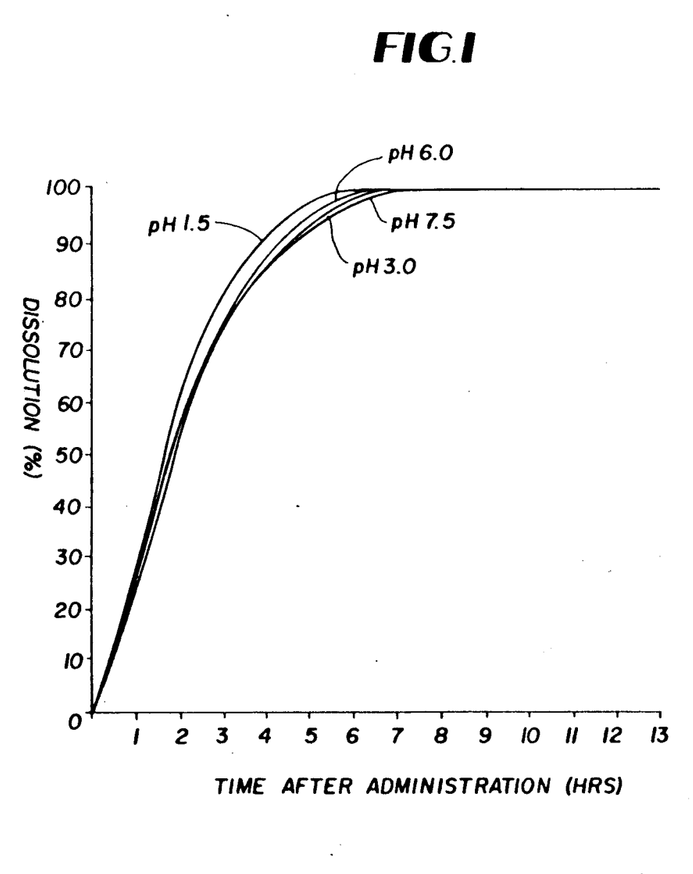
FIG. 1 is a graph showing dissolution rates in curves plotting the percentage dissolution against time after administering at each pH of 1.5, 3.0, 6.0 and 7.5, for the product of Example 1.
Figure 2:
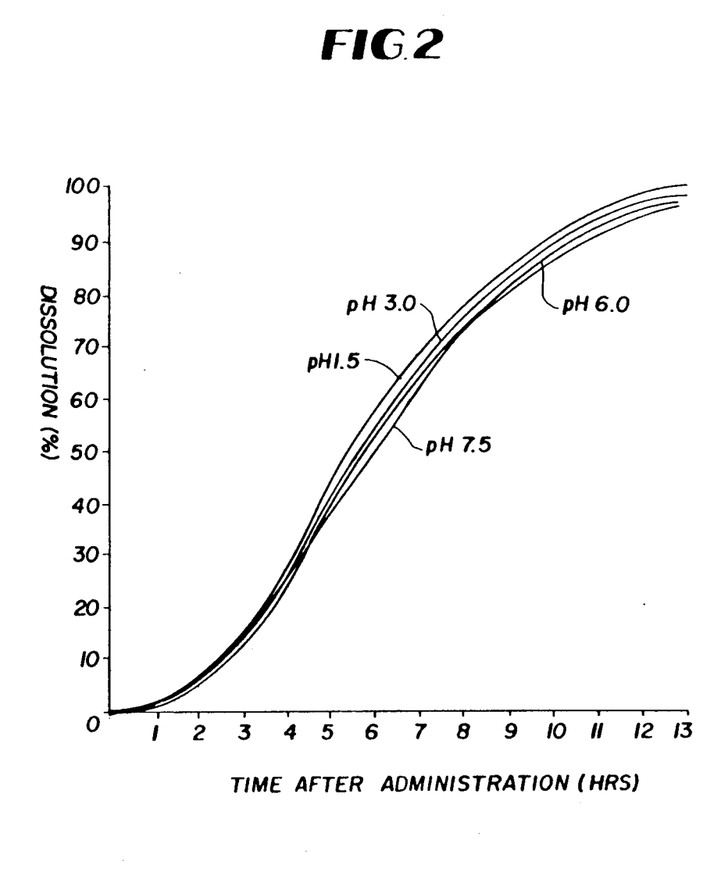
FIG. 2 is a graph as in FIG. 1 for the product of Example 2.
Figure 3:
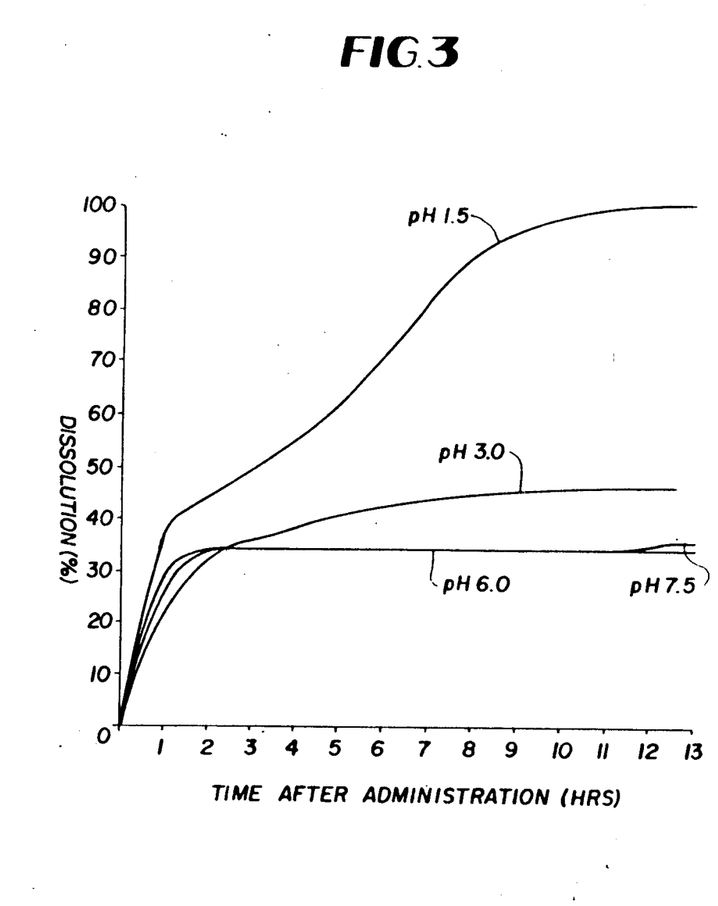
FIG. 3 is a graph as in FIG. 1 for the product of Example 3.

The dissolution rates of the three quinidine products prepared respectively in Examples 1, 2 and 3 are shown in FIGS. 1, 2 and 3. These figures show the dissolution rates in a curve plotting the percentage dissolution against the time after administration in hours, at each pH of 1.5, 3.0, 6.0 and 7.5. It can be seen from FIG. 3, where no pH adjusting agent is used, that the dissolution rate varies with the pH of the medium in which the dissolution is carried out. However, when a pH adjusting agent is used, the dissolution rate is independent of the pH of the dissolution medium.

Figure 4:
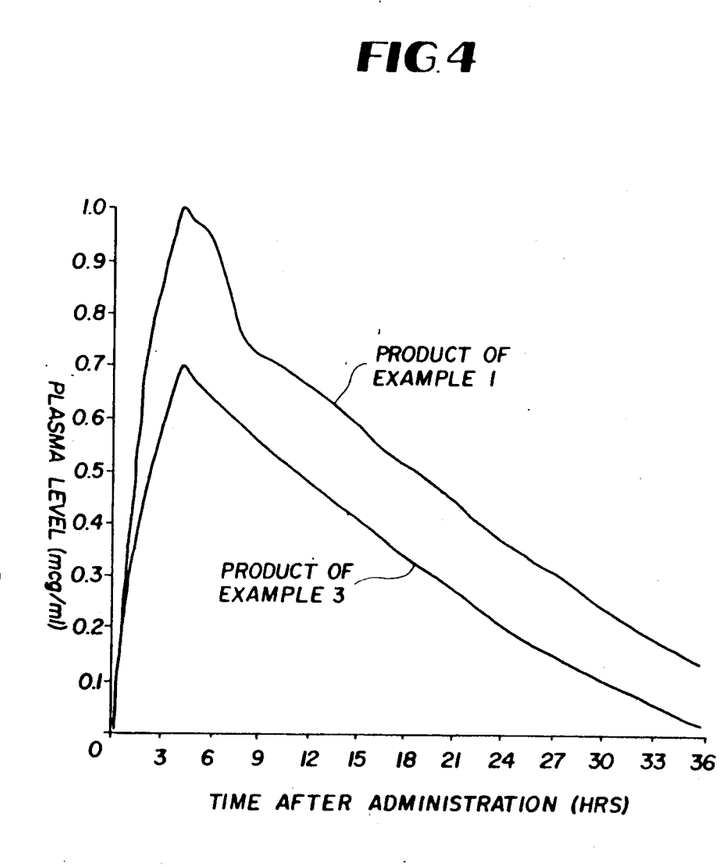
FIG. 4 is a graph having curves comprising plasma levels of drug as a function of time after administration as a mean of the total subjects tested for the product of Example 1 and for the product of Example 3.

The plasma levels of drug which are achieved with the pH-controlled product of Example 1 were compared with the levels which are achieved with the product having no pH control in accordance with Example 3, by administering a dose of one of the two products of each of six human patients, and determining the blood levels of quinidine sulphate in each of those patients at 0, 1, 2, 3, 4, 6, 8, 12, 24, and 36 hours after administration. Subsequently, an equal dosage of the other product was administered to the same subjects, and the plasma levels were determined at the same intervals. FIG. 4 is a plot of the plasma levels in mcg/ml as a function of time after administration in hours as a means of the six subjects tested for each of the two formulations administered. It can be seen that the higher and more prolonged plasma levels are achieved with pH adjusted products relative to products that are found with the product containing no pH adjusting agent.

Figure 5:
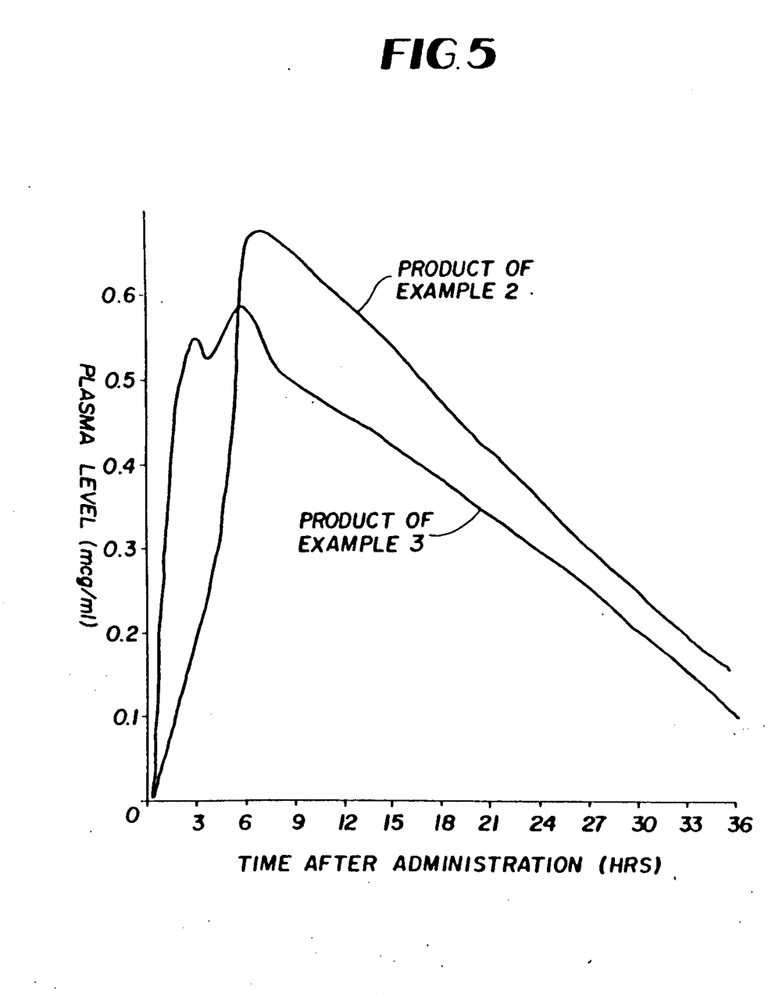
FIG. 5 is a graph as in FIG. 4 with curves comprising plasma levels as a function of time for the product of Example 2 with those for the product of Example 3.

FIG. 5 is a plot equivalent to that of FIG. 4 but comparing the products of Examples 2 and 3, using six different subjects. Again, higher and more prolonged plasma levels are achieved with the pH adjusted product relative to the levels that are found with the product containing no pH-adjusting agent.

EXPERIMENT 2

Figure 6:
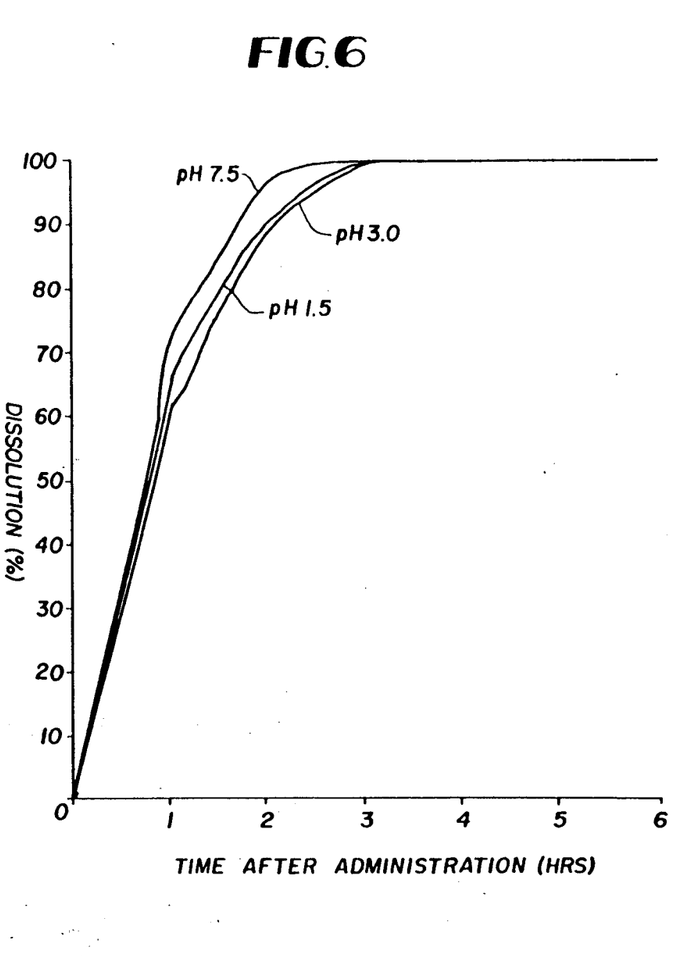
FIG. 6 is a graph showing dissolution rates in curves plotting the percentage dissolution against time after administration of each pH of 1.5, 3.0 and 7.5, for the product of Example 4.
Figure 7:
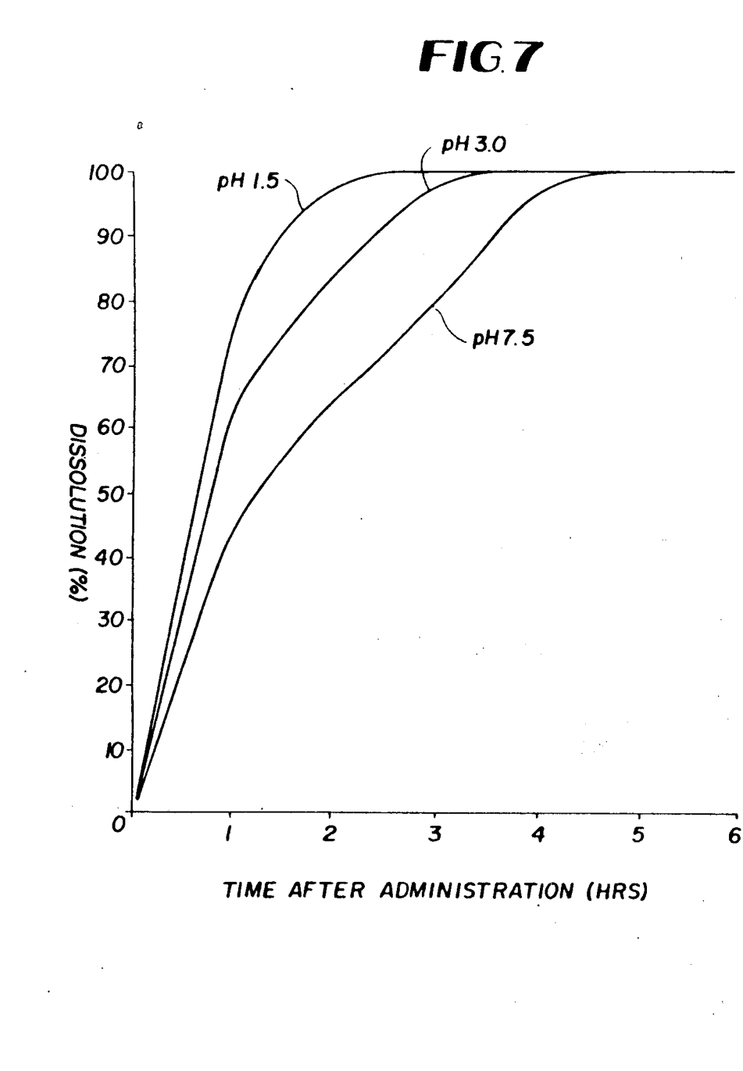
FIG. 7 is a graph as in FIG. 6 for the product of Example 2.

The dissolution rates (solubility) of the erythromycin products of Examples 4 and 5 are shown in FIGS. 6 and 7. FIG. 6 plots the percentage dissolution of erythromycin against the time after administration in hours at pH 1.5, 3.0 and 7.5. FIG. 6 relates to the dissolution of the product of Example 4, in which the pH adjusting agent (sodium citrate) is present in every application solution. FIG. 7 is the same plot for the product of Example 5, which product is identical to that of the product of Example 4 but for the absence of any pH-adjusting agent. It can be seen that where no pH-adjusting agent is used, the dissolution rate varies with the pH of the medium in which the dissolution is carried out. However, when a pH-adjusting agent is used, the dissolution rate is independent of the pH of the dissolution medium.

Figure 8:
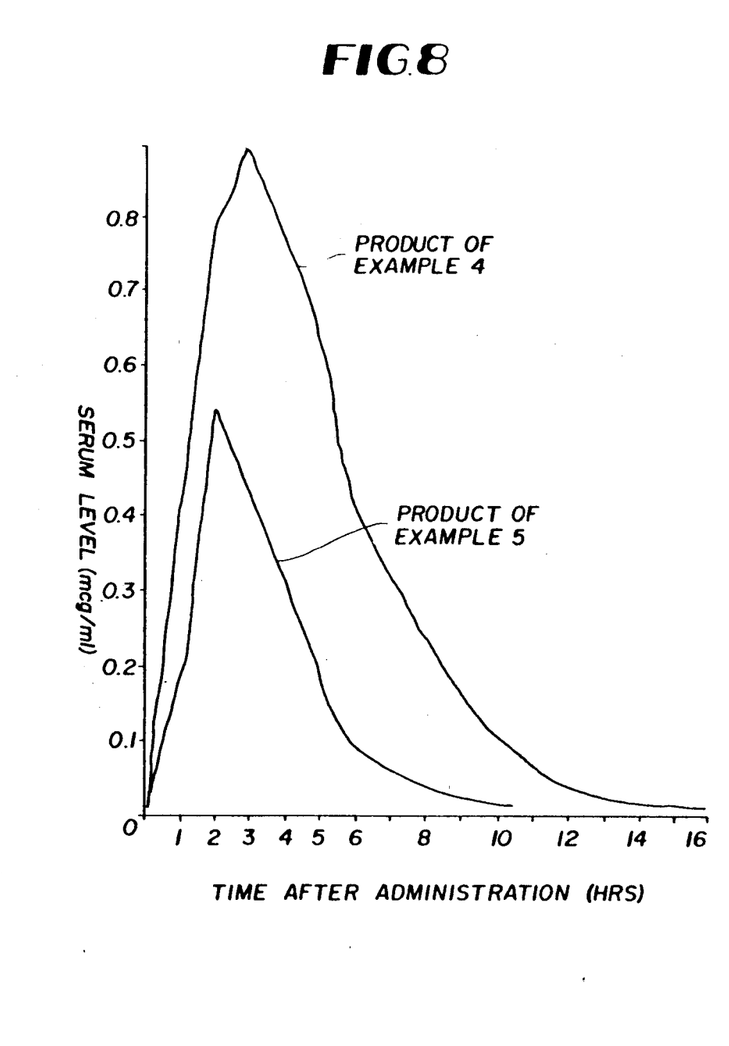
FIG. 8 is a graph having curves comprising plasma levels of drug as a function of time as a mean of the total subjects tested for the product of Example 4 and for the product of Example 5.
Figure 9:
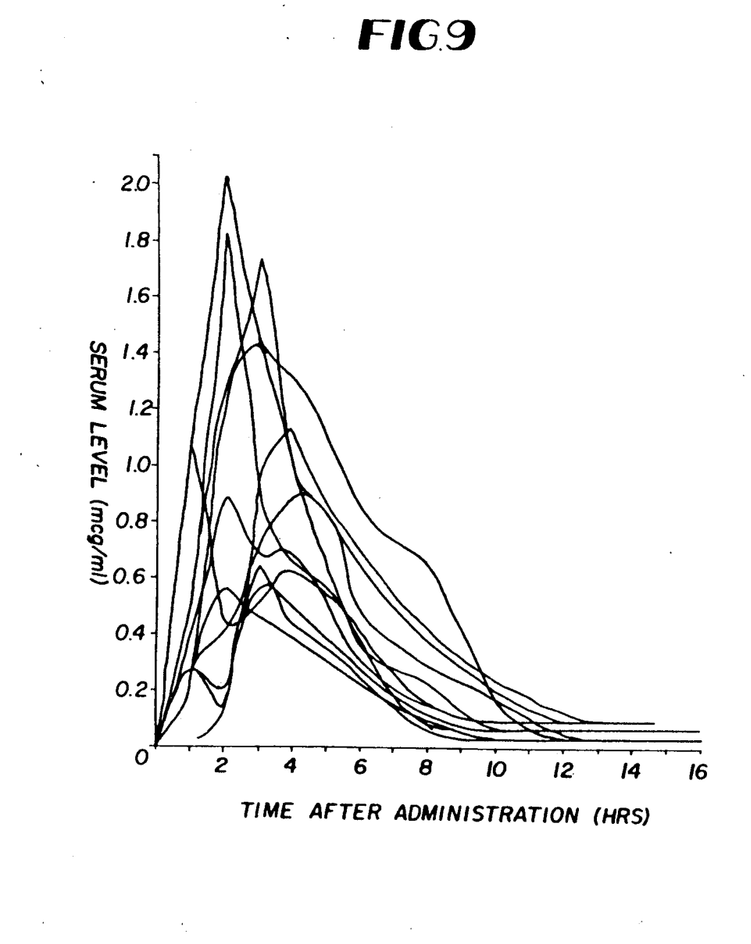
FIG. 9 is a graph having curves showing plasma levels of drug as a function of time for each of the twelve volunteer subjects, using the product of Example 4.
Figure 10:
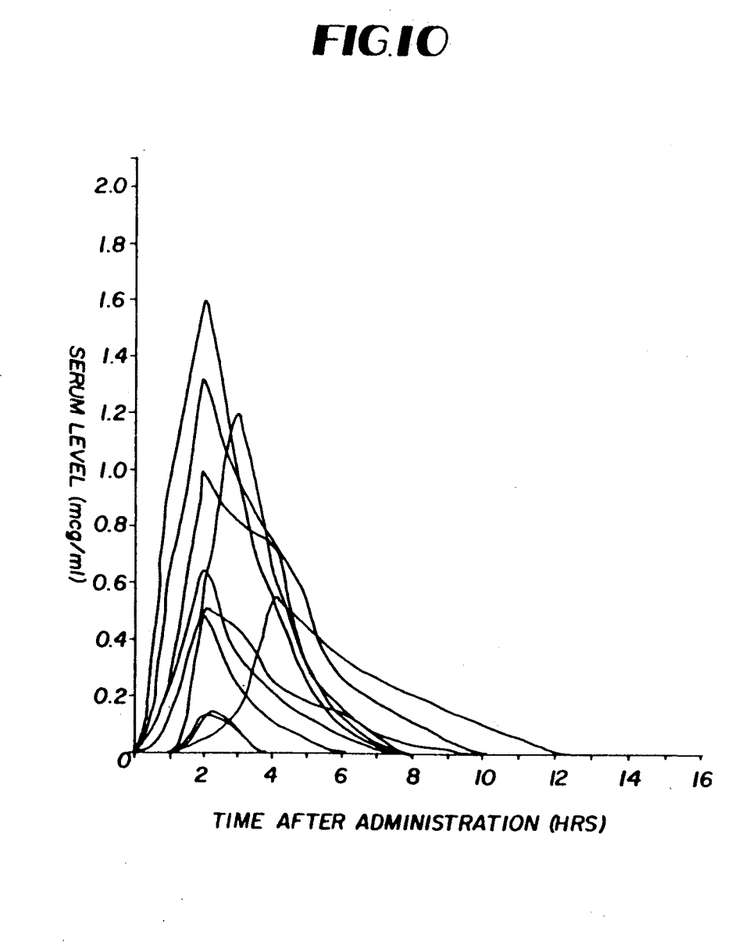
FIG. 10 is a graph as in FIG. 9 using the product of Example 5.

The plasma levels of drug which are achieved with the same two products (those of Examples 4 and 5) were compared by administering one of the two products to each of twelve volunteer subjects, and determining the plasma level of erythromycin at 0, 1, 2, 3, 4, 5, 6, 8, 10, 12, and 16 hours after administration. The other product is then administered to the same twelve subjects and the plasma levels of erythromycin determined at the same intervals. FIG. 8 shows the mean serum levels for the twelve subjects in mcg/ml plotted against time after administration in hours. FIG. 9 shows a similar graph in which the blood plasma level curves for each of the twelve subjects are plotted, in which the product administered is the product of Example 4, and FIG. 10 is the equivalent plot for the twelve subjects in which the pharmaceutical administered is the product of Example 5.

EXPERIMENT 3

Figure 11:
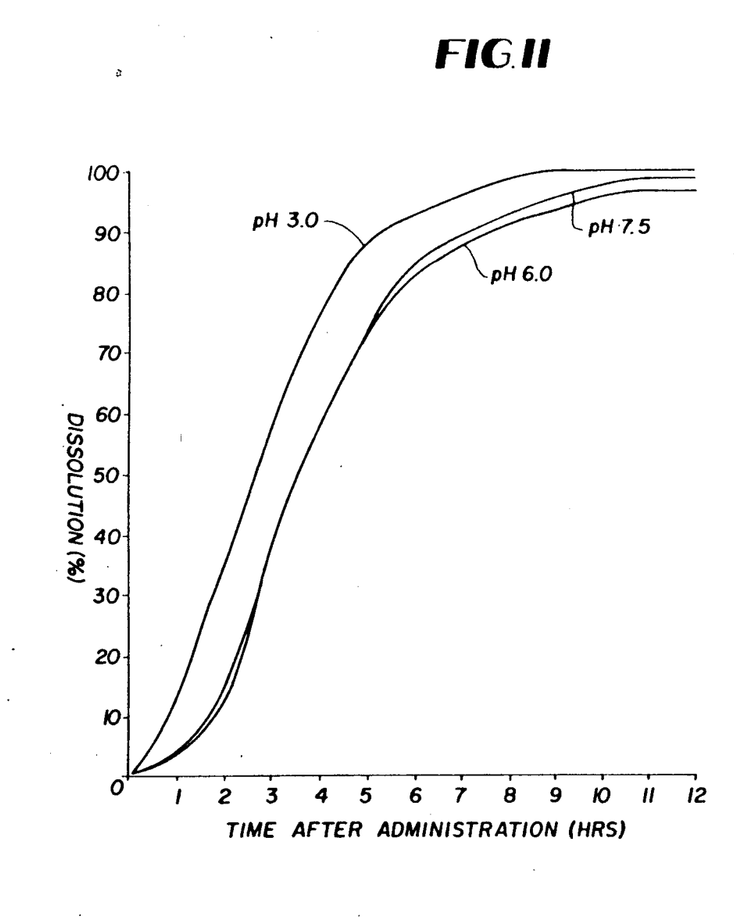
FIG. 11 is a graph showing dissolution rates in curves plotting the percentage dissolution against time after administration of each pH of 1.5, 3.0 and 7.5, for the product of Example 6.
Figure 12:
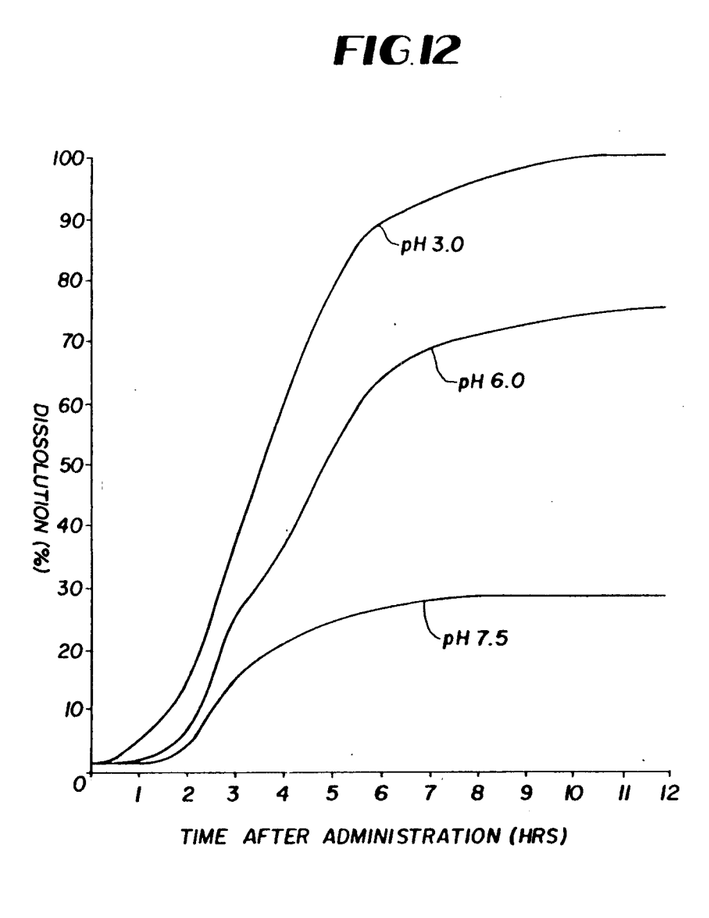
FIG. 12 is a graph as in FIG. 11 for the product of Example 7.

The dissolution rates of the dipyridamole products of Examples 6 and 7 are plotted respectively in FIGS. 11 and 12. The dissolution rates for each product were carried out at pH 3.0, 6.0 and 7.5. The plots show the percentage dissolution as a function of time after administration in hours. It can be seen that the dissolution rate is considerably more independent of the pH of the dissolution medium when pH-adjusting agents are used (FIG. 11), than in the absence of pH-adjusting agents (FIG. 12).

Figure 13:
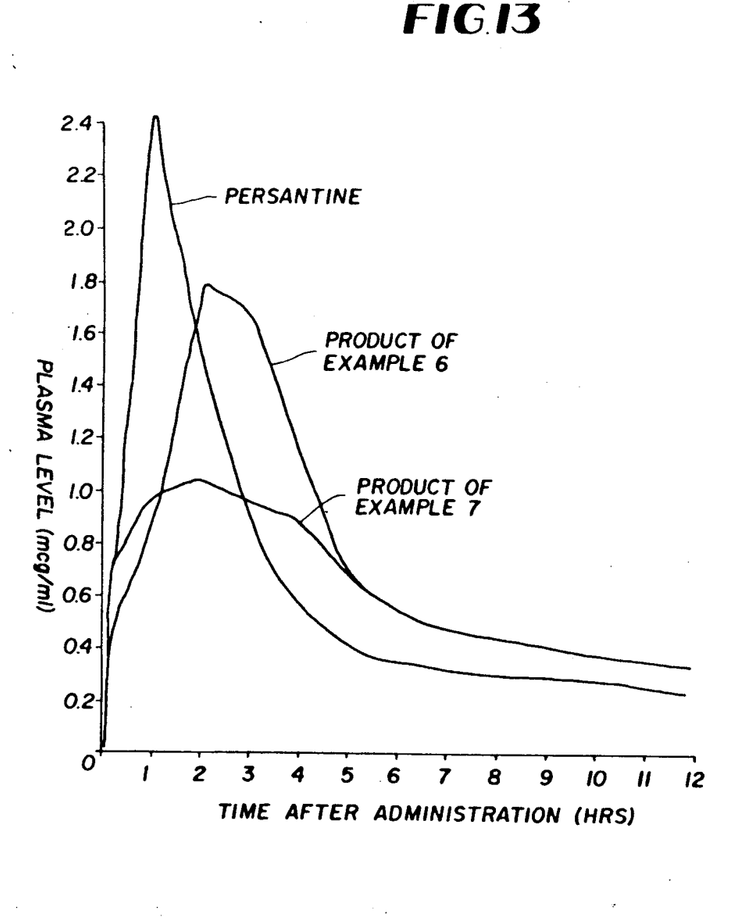
FIG. 13 is a graph having curves showing plasma levels of drug as a function of time as a mean of the total number of subjects tested for the product of Example 6, the product of Example 7 and the conventional tablet Persantine.

The plasma levels of dipyridamole in each of ten human volunteers were determined at 0, 1, 2, 3, 4, 5, 6.5, 9 and 12 hours after administration using the product of Example 6, containing pH-adjusting agent, and the product of Example 7, without pH-adjusting agent. As a comparison, a similar test was run on the same ten subjects using persantine which is a product of Boehringer Ingelheim Ltd. and which is a sugar coated tablet of dipyridamole. The mean plasma levels in mcg/ml for these three drug formulations are plotted against time after administration in hours in FIG. 13. It can be seen from the plasma level profile that improved levels are achieved with the pH controlled product of the present invention.

EXPERIMENT 4

Figure 14:
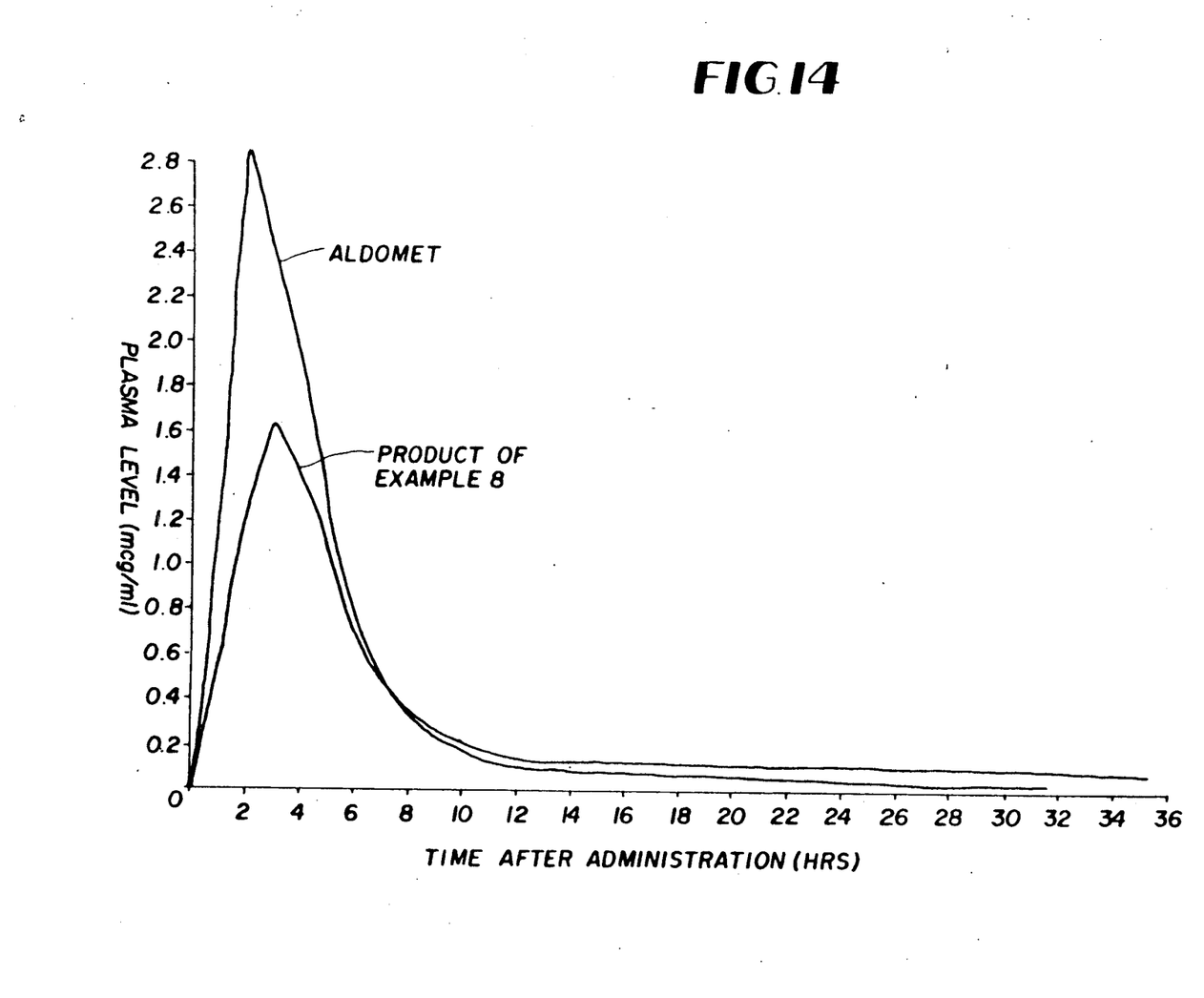
FIG. 14 is a graph as in FIG. 13 with curves for the product of Example 8 and the commercial tablet Aldomet.

The plasma levels of alpha-methyldopa prepared in accordance with Example 8 were determined by administering the drug to six human volunteer subjects, and determining the blood plasma level in mcg/ml after 0, 1, 2, 3, 4, 5, 6, 7, 8, 10, 12, 24 and 36 hours. The same test was conducted on the same volunteers using the commercial alpha-methyldopa product Aldomet, a product of Merck, Sharpe & Dohme division of Merck & Co., Inc. Aldomet tablets are 250 mg tablets of methyldopa which are film-coated. The mean blood levels in mcg/ml of each of the six subjects as a function of time after administration in hours with separate curves for each of the two products, are set forth in FIG. 14. Note the much steadier release profile with the pH-adjusted product relative to the levels that are found with the commercial product.

EXPERIMENT 5

Figure 15:
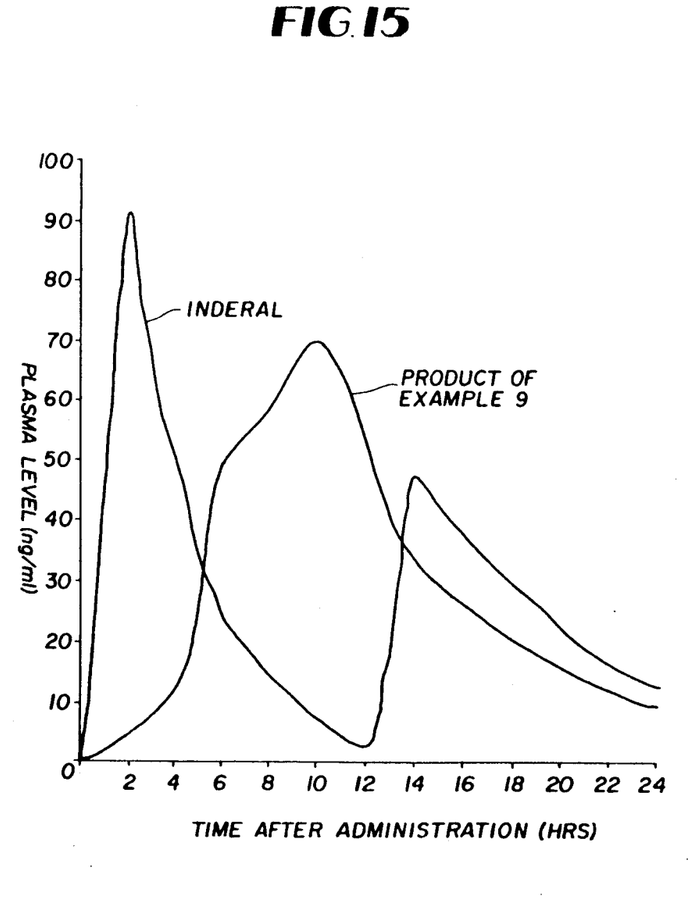
FIG. 15 is a graph as in FIG. 13 with curves for the product of Example 9 and the commercial tablet Inderal.

Blood plasma levels were determined in each of six volunteer subjects at 0, 2, 3, 4, 5, 6, 8, 10, 12, 13, 14, 15, 16, 24 and 36 hours after administration of the product of Example 9, and the same test was conducted on the same subjects using the commercial product Inderal, a product of Ayerst laboratories, Division of American Home Products Corporation. Inderal is a tablet of propranolol HCl. FIG. 15 shows the mean plasma levels for the six subjects using each of the two drugs in ng/ml as a function of time after administration in hours. Again, the steadier release profile for the pH-adjusted product of the present invention is to be noted.

EXPERIMENT 6

Figure 16:
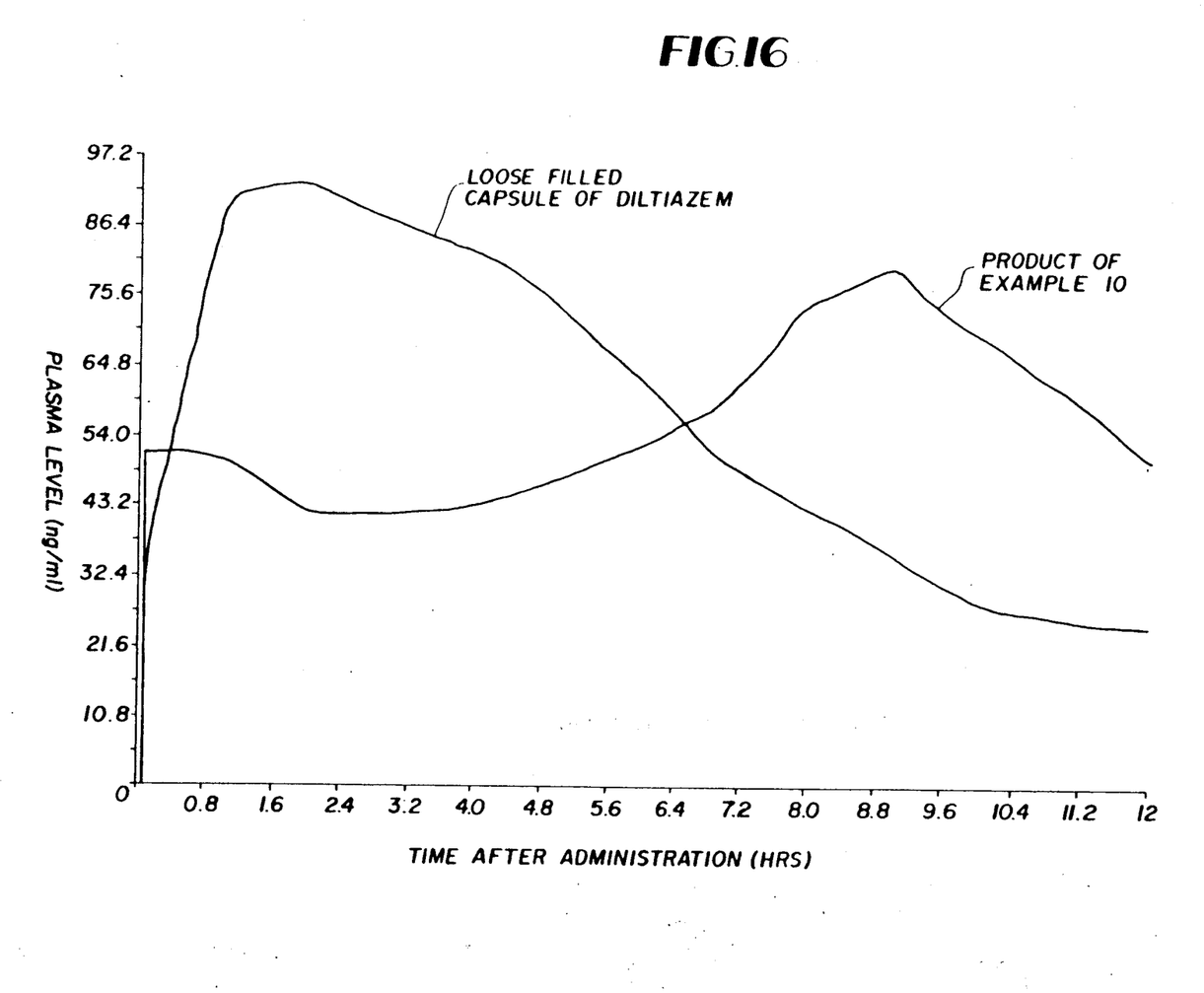
FIG. 16 is a graph as in FIG. 13 with curves for the product of Example 10 and loose filled capsules of diltiazem.

The blood plasma levels of the product of Example 10 was compared with that obtained using 60 mg loose filled capsules of diltiazem by administering one of the two formulations to six volunteers, and determining the blood plasma levels after 0, 1, 2, 3, 4, 5, 6, 7, 8, 9, 10, 11, and 12 hours. The same six volunteers were then administered the other of the two formulations and the blood plasma levels determined in the same intervals. The results of this comparison are shown in FIG. 16, in which the plasma levels in ng/ml as a function of time after administration in hours is shown as a mean of the six subjects, with separate curves for each of the two drugs. The product of the present invention shows a steadier and more prolonged blood level profile than the control.

EXPERIMENT 7

Figure 17:
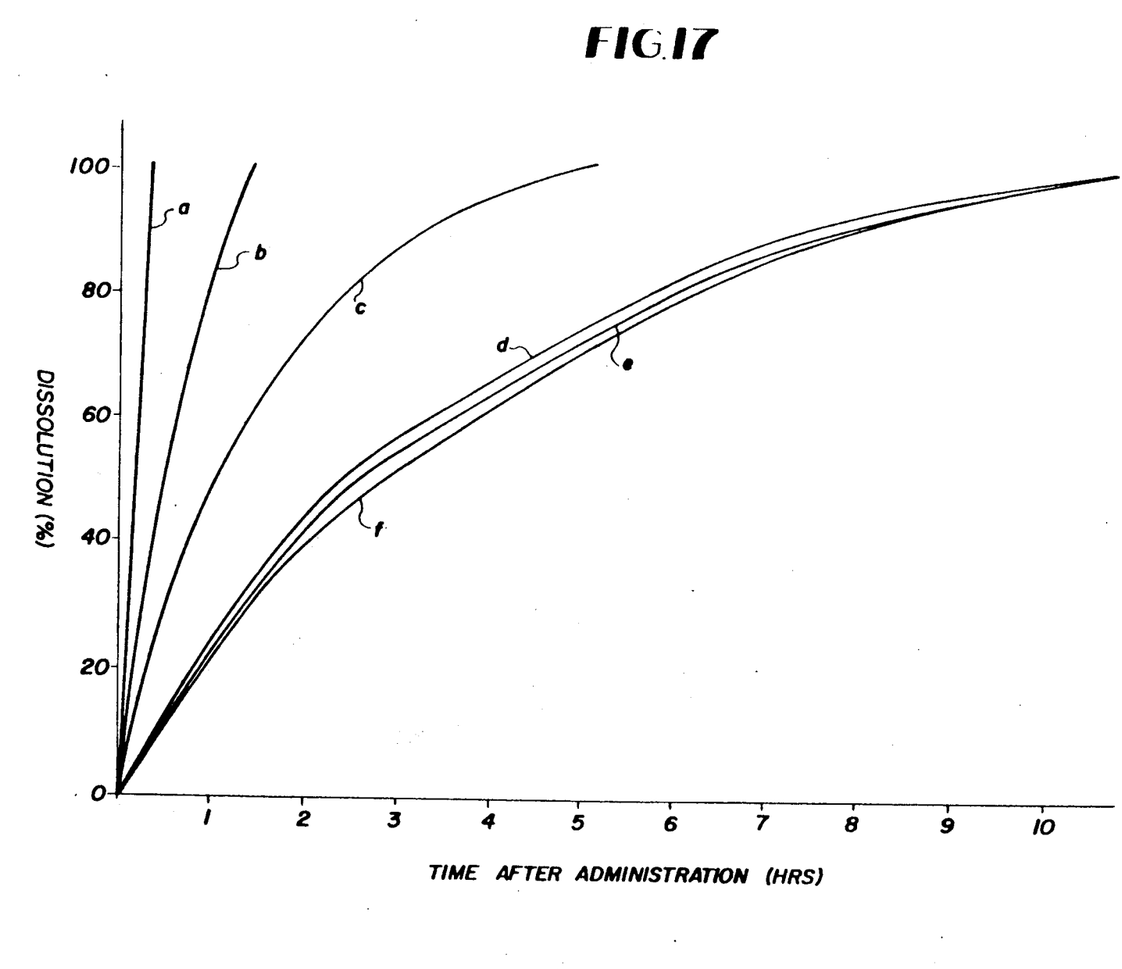
FIG. 17 is a graph showing dissolution rates in curves plotting the percentage dissolution against time after administration at each pH of 1.5, 3.0 and 6.0 for the product of Example 11 (curves d-f) and a commercial product (curves a-c).

FIG. 17 depicts the dissolution of indomethancin. The curves a, b and c are those of commercial indomethacin ("INDOCID") of Merck, Sharp and Dohme), while the curves d, e and f show the dissolutions of the pharmaceutical form according to Example 11. Curve a represents the dissolution as a function of time at pH 6, curve b represents dissolution at pH 3, and curve c represents dissolution at pH 1.5 of commercial indomethacin. This level of dissolution is heterogeneous and depends on the pH of the medium. The behavior is quite different with the pharmaceutical form according to Example 11. The dissolution is uniform and independent of pH: the three curves d (pH 1.5), e (pH 3) and f (pH 6) practically merge.

Table I below summarizes the blood plasma levels measured in 4 volunteers to whom were administered 15 mg of product according to Example 11 and a commercial product (the results are expressed in mcg/ml of blood plasma).

Table I shows clearly the uniformity of the results obtained with the pharmaceutical forms according to Example 11, which results confirm the dissolution tests shown in FIG. 17.

TABLE I

| Product | Time (in hours) | 1 | 2 | 3 | 4 | Average | Standard Deviation |
|---|---|---|---|---|---|---|---|
| according to the invention | 0 | 0 | 0 | 0 | 0 | 0 | 0 |
|  | 1 | 2.293 | 3.013 | 2.347 | 1.693 | 2.337 | 0.54 |
|  | 2 | 1.027 | 1.647 | 1.347 | 1.093 | 1.279 | 0.28 |
|  | 3 | 0.507 | 0.880 | 0.800 | 1.060 | 0.812 | 0.23 |
|  | 4 | 0.293 | 0.560 | 0.547 | 0.827 | 0.557 | 0.22 |
|  | 5 | 0.180 | 0.330 | 0.533 | 0.493 | 0.384 | 0.16 |
|  | 6 | 0.113 | 0.180 | 0.513 | 0.480 | 0.322 | 0.20 |
| Commercial product (Persantine) | 0 | 0 | 0 | 0 | 0 | 0 | 0 |
|  | 1 | 0.233 | 3.427 | 3.500 | 0.140 | 1.825 | 1.89 |
|  | 2 | 0.800 | 1.493 | 1.467 | 0.847 | 1.152 | 0.38 |
|  | 3 | 0.480 | 0.860 | 0.730 | 0.724 | 0.699 | 0.15 |
|  | 4 | 0.267 | 0.447 | 0.410 | 0.600 | 0.431 | 0.14 |
|  | 5 | 0.160 | 0.267 | 0.240 | 0.380 | 0.262 | 0.09 |
|  | 6 | 0.113 | 0.160 | 0.130 | 0.227 | 0.158 | 0.05 |

It will be obvious to those skilled in the art that various changes may be made without departing from the scope of the invention and the invention is not to be considered limited to what is shown in the drawings and described in the specification.

What is claimed:

1. A sustained release composition comprising:
   (a) an excipient or coating selected from a group consisting of polyvinylpyrrolidone, shellac, waxes and syrups; and
   (b) at least one adjuster, said pH adjuster being selected from the group consisting of an organic acid, organic acid salt, an organic base, an inorganic base and a basic salt;
   wherein said excipient or coating composition surrounds a core comprising a medicament whose solubility varies with pH; and
   wherein the pH of said excipient or coating composition is adjusted to a desired pH by said pH adjuster to ensure that the rate of dissolution of said medicament is substantially independent of the pH of the environment in which dissolution occurs.

2. A delayed action programmed release pharmaceutical preparation of one or more medicament units suitable for oral administration, each unit comprising:
   (1) an inert core surrounded by at least one inner layer, wherein at least one of said inner layer(s) comprises (a) an active medicament, which medicament has a solubility which varies with pH and is basic or acidic; and (b) at least one pH adjuster means, said adjuster means is an organic acid or organic acid salt if said medicament is basic, or an inorganic base or a basic salt if said medicament is acidic, said pH adjuster means is present in an amount sufficient to insure that the rate of dissolution of said medicament is substantially independent of the pH of the environment in which dissolution occurs; and
   (2) said inner layer(s) surrounded by one or more inert outer coatings.

3. A sustained release composition of claim 1, wherein the unit is in the form of a pellet.

4. The sustained release composition of claim 1, wherein said active ingredient is a basic medicament selected from the group consisting of dipyridamole, cephalexin, cephalothin, cimetidine, methyldopa, cefazolin, propanolol, doxycycline, amoxycillin, propoxyphene, ampicillin, lincomycin, vincamine, clonidine, glafenine, disopyramide, clorazepate, cephalosporins, and rifamycin.

5. The sustained release composition of claim 1, wherein said medicament is dipyridamole.

6. The sustained release composition of claim 1, wherein said pH adjuster is an organic acid or an acid salt.

7. The sustained release composition of claim 1, wherein said core also comprises dipyridamole.

8. The sustained release composition of claim 1, wherein the medicament is acidic or acid hydrolyzable selected from the group consisting of ibuprofen, furosemide, indomethacin, spironolactine, diazepam, erythromycin, gentamicin, diclofenac, glibenclamide, althiazide, naproxen, allopurinol, sulfamethoxazole, prosultiamine, betmethasone, troleandomycin, clometacin, sulpiride, oxyphenbutazone and sulindac.

9. The sustained release composition of claim 1, wherein said medicament is indomethacin.

10. The sustained release composition of claim 1, wherein the pH adjuster is a base of basic salt.

11. The sustained release composition of claim 1, wherein said core comprises indomethacin.

12. A delayed action programmed release pharmaceutical preparation of one or more indomethacin units suitable for oral administration, each unit comprising:

(1) an inert core surrounded by at least one inner layer(s) wherein at least one said inner layer(s) comprises (a) acidic indomethacin having a solubility which varies with pH; and (b) a pH adjuster means comprising basic sodium citrate mixed with saccharose, said pH adjuster means present in an amount sufficient to insure the rate of dissolution of indomethacin is substantially independent of pH of the environment in which dissolution occurs; and (2) said inner layer(s) surrounded by one or more inert outer coatings comprised of polyvinylpyrrolidone and gum-lac.

13. A delayed action programmed release pharmaceutical preparation of one or more dipyridamole units suitable for oral administration, each unit comprising:

(1) a core surrounded by at least one inner layer(s) wherein at least one said inner layer(s) comprises (a) basic dipyridamole having a solubility which varies with pH; and (b) a pH adjuster means comprising citric acid mixed with saccharose, and citric acid being present in an amount sufficient to insure the rate of dissolution of said dipyridamole is substantially independent of pH of the environment in which dissolution occurs; and (2) said inner layer surrounded by one or more outer coatings of polyvinylpyrrolidone mixed with gum-lac.

14. A method of preparing a delayed action or controlled release pharmaceutical formulation comprising:

(a) applying a medicament whose solubility varies with pH to an inert core by means of an application solution to form a pellet;

(b) coating said pellet with one or more layers of an excipient or coating selected from the group consisting of polyvinyl pyrrolidone, shellac waxes and syrups which controls the release from said pellets of said medicaments; and (c) adjusting each of said medicament layer, said excipient and coating layers to an acid pH by means of at least one of an organic acid or organic acid salt if said medicament is a weak base, or a basic pH by means of at least one of an organic base, an inorganic base or a base salt if said medicament is a weak acid in order to render the rate of dissolution of said medicament from said pellet substantially independent of the pH of the environment in which dissolution occurs.

15. A sustained release composition, comprising two or more layers, each comprising:

(a) an excipient selected for a group consisting of polyvinyl pyrrolidone, shellac, waxes and syrups; and (b) at least one pH adjuster, said pH adjuster being selected from the group consisting of an organic acid, organic acid salt, an organic base, an inorganic base and a basic salt;

wherein said excipient or coating composition surrounds a core comprising a medicament whose solubility varies with pH; and wherein the pH of each of said layers is adjusted to a desired pH by said pH adjuster to ensure that the rate of dissolution of said medicament is substantially independent of the pH of the environment in which dissolution occurs.

16. A delayed action programmed release pharmaceutical preparation of one or more medicament units suitable for oral administration, each unit comprising:

(1) an inert core surrounded by an inner layer(s), wherein each of said inner layer(s) comprises (a) an active medicament, which medicament has a solubility which varies with pH and is basic or acidic; and (b) at least one pH adjuster means, said adjuster means selected from the group consisting of an organic acid, organic acid salt if said medicament is basic, or from the group consisting of an inorganic base or a basic salt if said medicament is acidic, said pH adjuster means being present in the core and each inner surrounding layer in an amount sufficient to insure that the rate of dissolution of said medicament is substantially independent of the pH of the environment in which dissolution occurs; and (2) said inner layer(s) surrounded by one or more inert outer coatings also containing said pH adjuster.

* * * * *